(12) United States Patent
Tomellini et al.

(10) Patent No.: US 10,012,632 B2
(45) Date of Patent: *Jul. 3, 2018

(54) PERSONAL SUBSTANCE DETECTION FIELD TEST KIT

(71) Applicant: LINDON GROUP, INC., East Providence, RI (US)

(72) Inventors: Dalita Tomellini, Rehoboth, MA (US); Melinda Penney, Providence, RI (US); Phil Brooks, Franklin, MA (US)

(73) Assignee: Lindon Group, Inc., East Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,719

(22) Filed: Jan. 23, 2017

(65) Prior Publication Data

US 2017/0131258 A1    May 11, 2017

Related U.S. Application Data

(63) Continuation of application No. 13/748,037, filed on Jan. 23, 2013, now Pat. No. 9,551,695.

(60) Provisional application No. 61/590,150, filed on Jan. 24, 2012.

(51) Int. Cl.
*B65D 43/16* (2006.01)
*G01N 33/22* (2006.01)
*G01N 21/78* (2006.01)

(52) U.S. Cl.
CPC ........... *G01N 33/227* (2013.01); *G01N 21/78* (2013.01); *G01N 2201/0221* (2013.01)

(58) Field of Classification Search
CPC ........ G01N 31/22; B65D 45/22; B65D 45/20; B65D 45/16; B65D 45/02; B65D 43/163; B65D 43/16; B65D 43/14
USPC ....... 73/865.9; 220/326, 324, 316, 315, 827, 220/810; 292/300, 303, 304, 80, 87–89, 292/91, DIG. 11, DIG. 49
See application file for complete search history.

(56) References Cited

U.S. PATENT DOCUMENTS

| | | |
|---|---|---|
| 2,643,148 A | 6/1953 | Gaston |
| 3,811,747 A | 5/1974 | Levin |
| 3,893,725 A | 7/1975 | Coulter et al. |
| 4,111,476 A | 9/1978 | Jacobs |
| 4,955,957 A | 9/1990 | Homes |

(Continued)

OTHER PUBLICATIONS

DropEx, Plexus Scientific, http://www.plexsci.com/products/detection-kits/explosive-detection/dropex- /, accessed May 24, 2011.

(Continued)

*Primary Examiner* — Peter Macchiarolo
*Assistant Examiner* — Alexander Mercado
(74) *Attorney, Agent, or Firm* — Carter, DeLuca, Farrell & Schmidt, LLP

(57) ABSTRACT

A personal-sized, portable explosive detection field test kit (ETK) and related methods of use. Embodiments of the disclosed ETK include a case having a closing system featuring three levels of closure which retain the case cover securely in a closed position until ready for use, while being easily opened when necessary. The ETK instructions are permanently attached to the case to prevent loss. The case includes retention features which retain the kit components until needed and protects them against loss or damage. The ETK includes one or more test tubes that are color coded and include abbreviated instructions.

20 Claims, 5 Drawing Sheets

(56) References Cited

U.S. PATENT DOCUMENTS

| | | | |
|---|---|---|---|
| 5,193,701 | A | 3/1993 | Bush et al. |
| 5,480,612 | A | 1/1996 | Margalit |
| 5,738,238 | A | 4/1998 | Yang |
| 6,050,404 | A | 4/2000 | Lee |
| 8,889,421 | B1 | 11/2014 | Ouellette et al. |
| 9,551,695 | B2 | 1/2017 | Tomellini et al. |
| 2002/0150504 | A1 | 10/2002 | Nunes et al. |
| 2003/0015534 | A1 | 1/2003 | Lown et al. |
| 2003/0038047 | A1 | 2/2003 | Sleva et al. |
| 2005/0004500 | A1 | 1/2005 | Rosser et al. |
| 2011/0287402 | A1 | 11/2011 | Sanford |

OTHER PUBLICATIONS http://ep.yimg.com/ay/security2020/drop-ex-plus-explosives-detection-sprays-these-explosives-detections-sprays-are-able-to-detect-chlorate-based-exp- losives-and-peroxide-based-explosives-drop-ex-plus-is-a-new-product-that-a-ctually-is-an-extension-to-the-dropex-kit-8.jpg, accessed Jun. 8, 2015.

PERSONAL SUBSTANCE DETECTION FIELD TEST KIT

CROSS-REFERENCE TO RELATED APPLICATION

This application is a continuation application of U.S. patent application Ser. No. 13/748,037, filed Jan. 23, 2013, now U.S. Pat. No. 9,551,695, and claims priority from, and the benefit of, U.S. Provisional Application Ser. No. 61/590,150, filed Jan. 24, 2012, the entirety of which are hereby incorporated by reference herein for all purposes.

BACKGROUND

Testing for substances such as explosives is a task which must be conducted effectively and reliably, as the consequence of a testing failure can be catastrophic. Explosives detection field test kits, or ETKs, are widely used by military, police, and security forces to detect the presence of explosive substances and precursor chemicals. ETKs play a vital role in maintaining order and protecting life and property. Other variations of test kits are employed by security personnel to detect the presence of, for example, illicit drugs, pathogens, chemicals, and the like.

Though ETKs are widely used, end users of such field test kits typically do not use them on a regular basis, and are therefore at a disadvantage because the practice and skill which comes from regular use is not availing to the typical user. In some cases users have little or no prior training with respect to the use of such testing kits. Often, users are unable to successfully utilize the test kit because the instructions may be lost or too difficult to comprehend at the point of use. This is particularly problematic in combat or other high-stress situations, where manual dexterity, cognitive function, or situational awareness may be impaired.

SUMMARY

The present disclosure is directed to an improved explosives detection field test kit having features which advance the state of the art for reliable, consistent, and successful explosive testing and significantly reduce the likelihood of improper utilization of the kit which may lead to a testing failure.

In one aspect, a portable substance detection field test kit is disclosed. The disclosed test kit includes a top cover having a hinge side and a latch side, and includes an instruction card fixed to an inner surface of the top cover, a pocket adapted to retain one or more sheets of test paper, and a ridge extending from the latch side of the top cover. The test kit includes a bottom cover having a hinge side and a latch side, and includes at least one cradle on an inner surface thereof configured to selectively retain a drip tube, and a latch face extending from the latch side thereof having a snap rib protruding from the latch face. The top cover and bottom cover are joined by a hinge along the respective hinge sides thereof forming a housing having an open position wherein the latch sides of the top cover and bottom cover are separated, and a closed position wherein the latch sides of the top cover and bottom cover are joined. The disclosed test kit includes at least one drip tube, at least one sheet of test paper adapted to collect a substance sample, and a latch assembly. The latch assembly includes a latch lever having an open position and a closed position, a stop rib operatively associated with the latch lever and configured to engage the underside of the latch face when the latch lever is in a closed position, and a first hook and loop fastener and a mating second hook and loop fastener. The first hook and loop fastener is disposed on an inner surface of the latch lever and the second hook and loop fastener is disposed on a mating surface of the bottom cover, and the first and second hook and loop fasteners engage when the latch lever is in a closed position.

In some embodiments, when the housing is in a closed position the snap rib of the bottom cover and the ridge of the top cover are cooperatively engaged. In some embodiments, the latch lever is joined to the top cover by a hinge. In some embodiments, a gasket is disposed between the top cover and the bottom cover. In some embodiments, the top cover includes a contoured portion defined on an inner surface thereof. In some embodiments, the contoured portion is concave. In some embodiments, the depth of the concave contoured portion is in a range of about 1/16 inches to about 1/2 inches. In some embodiments, the at least one drip tube contains a reagent solution configured to expose the presence of a targeted substance by causing an initial color of a test sample to change to a predetermined color when the reagent solution is applied to the test sample. In some embodiments, the drip tube includes a label having a color indicating the predetermined color. In some embodiments, the targeted substance is selected from the group consisting of TNT, DNT, TNB, tetryl, picric Acid, NG, PETN, RDX, HMX, NC, C4, Semtex, smokeless powder, ammonium nitrate, potassium nitrate, black powder, ANFO, inorganic chlorates, hypochlorite, bromates, organic peroxides, TATP, DADP, and HMTD, ammonium; urea nitrate, THC, an opiate, cocaine, methamphetamine, oxycodone, MDMA, LSD, mescaline, psilocybin, and scopolamine.

In another aspect, a portable container is disclosed. The disclosed container includes a top cover having a hinge side and a latch side, and a ridge extending from the latch side of the top cover. The bottom cover has a hinge side and a latch side, and a latch face extending from the latch side thereof having a snap rib protruding from the latch face. The top cover and bottom cover are joined by a hinge along the respective hinge sides thereof forming a housing having an open position wherein the latch sides of the top cover and bottom cover are separated and a closed position wherein the latch sides of the top cover and bottom cover are joined. The disclosed container includes a latch assembly that includes a latch lever having an open position and a closed position, a stop rib operatively associated with the latch lever and configured to engage the underside of the latch face when the latch lever is in a closed position, and a first hook and loop fastener and a mating second hook and loop fastener. The first hook and loop fastener is disposed on an inner surface of the latch lever, and the second hook and loop fastener is disposed on a mating surface of the bottom cover. The first and second hook and loop fasteners engage when the latch lever is in a closed position.

In some embodiments, when the housing of the disclosed portable container is in a closed position, the snap rib of the bottom cover and the ridge of the top cover are cooperatively engaged. In some embodiments, the latch lever is joined to the top cover by a hinge. In some embodiments, a gasket is disposed between the top cover and the bottom cover. In some embodiments, the top cover further comprising a contoured portion defined on an inner surface thereof. In some embodiments, the contoured portion is concave. In some embodiments, the depth of the concave contoured portion is in a range of about 1/16 inches to about 1/2 inches.

In yet another aspect, a method of conducting a test to detect the presence of a targeted substance is disclosed. The method includes providing a portable substance detection field test kit having a top cover having a hinge side and a latch side, an instruction card fixed to an inner surface of the top cover, a pocket adapted to retain one or more sheets of test paper, and a ridge extending from the latch side of the top cover. The provided test kit includes a bottom cover having a hinge side and a latch side and having at least one cradle on an inner surface thereof configured to selectively retain a drip tube, and a latch face extending from the latch side thereof having a snap rib protruding from the latch face. The top cover and bottom cover are joined by a hinge along the respective hinge sides thereof forming a housing having an open position wherein the latch sides of the top cover and bottom cover are separated and a closed position wherein the latch sides of the top cover and bottom cover are joined. The provided test kit includes at least one drip tube containing a reagent solution configured to expose the presence of a targeted substance by causing an initial color of a test sample to change to a predetermined color when the reagent solution is applied to the test sample, at least one sheet of test paper adapted to collect a substance sample, and a latch assembly. The latch assembly includes a latch lever having an open position and a closed position, a stop rib operatively associated with the latch lever and configured to engage the underside of the latch face when the latch lever is in a closed position, and a first hook and loop fastener and a mating second hook and loop fastener. The first hook and loop fastener is disposed on an inner surface of the latch lever and the second hook and loop fastener is disposed on a mating surface of the bottom cover. The first and second hook and loop fasteners engage when the latch lever is in a closed position. The method includes removing a sheet of test paper from the pocket, wiping a surface to be tested with the test paper, removing a drip tube corresponding to the desired substance for which the test is being conducted from its respective cradle, dispensing the reagent solution from the drip tube onto the test paper, observing a color change on the test paper, and concluding that the targeted substance is present in the test sample if the color of the test paper changes to a predetermined color. In some embodiments, the disclosed method includes comparing the color change of the test paper to a color sample provided on a label affixed to the drip tube. In some embodiment, the method includes detecting a targeted substance selected from the group consisting of TNT, DNT, TNB, tetryl, picric Acid, NG, PETN, RDX, HMX, NC, C4, Semtex, smokeless powder, ammonium nitrate, potassium nitrate, black powder, ANFO, inorganic chlorates, hypochlorite, bromates, organic peroxides, TATP, DADP, and HMTD, ammonium; urea nitrate, THC, an opiate, cocaine, methamphetamine, oxycodone, MDMA, LSD, mescaline, psilocybin, and scopolamine.

BRIEF DESCRIPTION OF THE DRAWINGS

Example embodiments in accordance with the present disclosure are described herein with reference to the drawings wherein.

DETAILED DESCRIPTION

Figure 1:
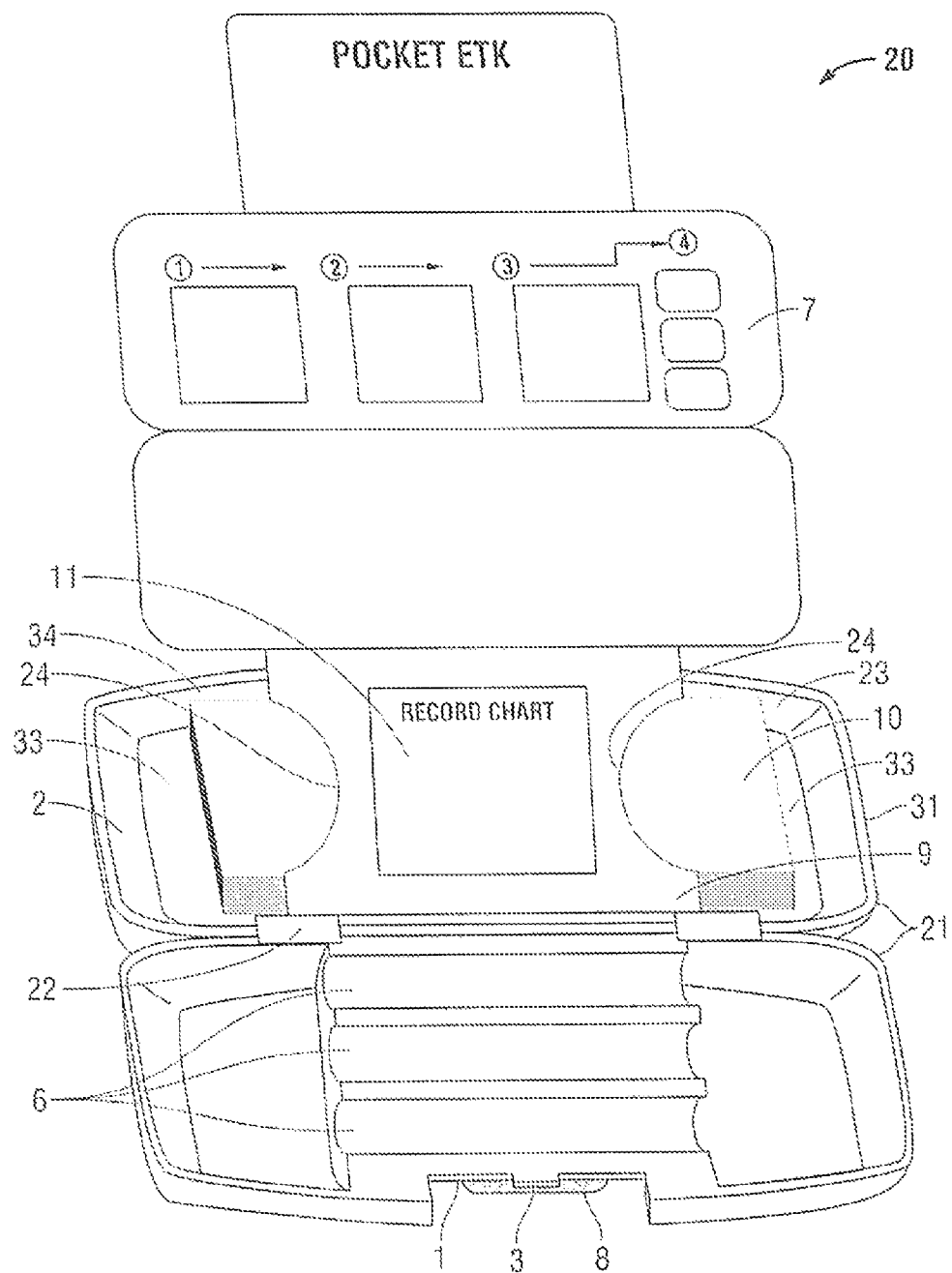
FIG. 1 is a top view of an embodiment of an ETK in accordance with the present disclosure wherein the housing is in an open position and an instruction card is shown extending from the cover.

Particular embodiments of the present disclosure are described hereinbelow with reference to the accompanying drawings; however, it is to be understood that the disclosed embodiments are merely examples of the disclosure, which may be embodied in various forms. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In addition, as used herein, terms referencing orientation, e.g., "top", "bottom", "up", "down", "left", "right", "clockwise", "counterclockwise", and the like, are used for illustrative purposes with reference to the figures and features shown therein. It is to be understood that embodiments in accordance with the present disclosure may be practiced in any orientation without limitation. In this description, as well as in the drawings, like-referenced numbers represent elements which may perform the same, similar, or equivalent functions.

The present disclosure is directed to an explosive test kit (ETK) having improved features which enable the kit to be easily and readily used by any user regardless of skill level, including without limitation, an occasional user, an untrained user, a user experiencing the effects of stress, and the like. In one aspect of the present disclosure, the ETK includes instructions that are easily available and understandable. In some embodiments, the instructions are permanently attached to the case of the ETK. In another aspect, the disclosed ETK incorporates a rugged design having a latching system which does not inadvertently open when the ETK is jostled around in a pocket or bag, while enabling the user to readily open the ETK when necessary for use. In some embodiments, the latching system includes features which keep the case closed with three levels of closure, while still enabling a user to easily open the case. In still another aspect, the disclosed ETK is configured such that, once opened, that that the kit components do not fall out on their own.

Prior art personal-sized test kits lack color-coding and have unattached instructions that can be easily lost. Further, prior art test kits use no instructions on the component labels, such as labels of the test tube. In addition, prior art test kit store testing tubes in a manner (for example, in a vertical sleeve) that obscures the test tube label, requiring the user to blindly remove each tube until the desired tube is identified. Thus prior art test kits, when opened, present difficulties to the user who cannot quickly identify the various components and test tubes, and therefore must first locate, and then refer to, the instructions. If the instructions are missing, the ETK may be rendered useless unless the user has the instructions memorized. In critical situations where every second counts, these drawbacks may have serious consequences.

In a further aspect, the ETK utilizes a color-coding system wherein components of the ETK are color coded to correspond with similar color coding on an instruction sheet or card. In some embodiments, the individual components of the ETK include abbreviated instructions, which may pertain to the specific component and/or to one or more of the other components of the kit. These improved features facilitate the rapid assimilation of ETK operational instructions by a user, enables the user to quickly identify ETK components, and enables successful utilization of the ETK to obtain accurate, consistent, and reliable results.

Embodiments of an ETK in accordance with the present disclosure are essentially failure-proof, at least in part because the instructions are permanently attached to the case, because the components do not fall out on their own, and because the test tubes are color coded and include abbreviated instructions.

Figure 2:
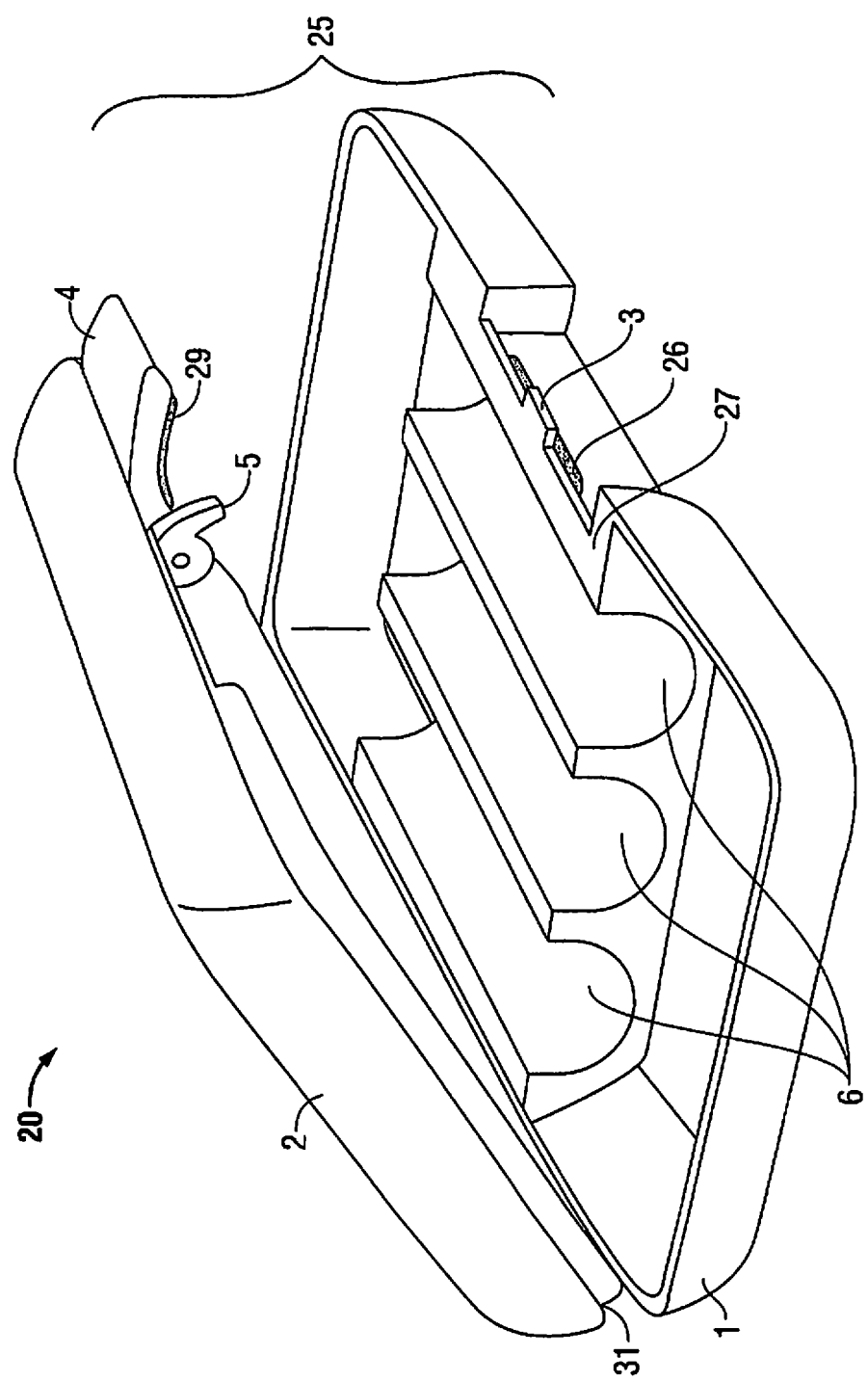
FIG. 2 is an oblique, side view of an embodiment of an ETK in accordance with the present disclosure.
Figure 3:
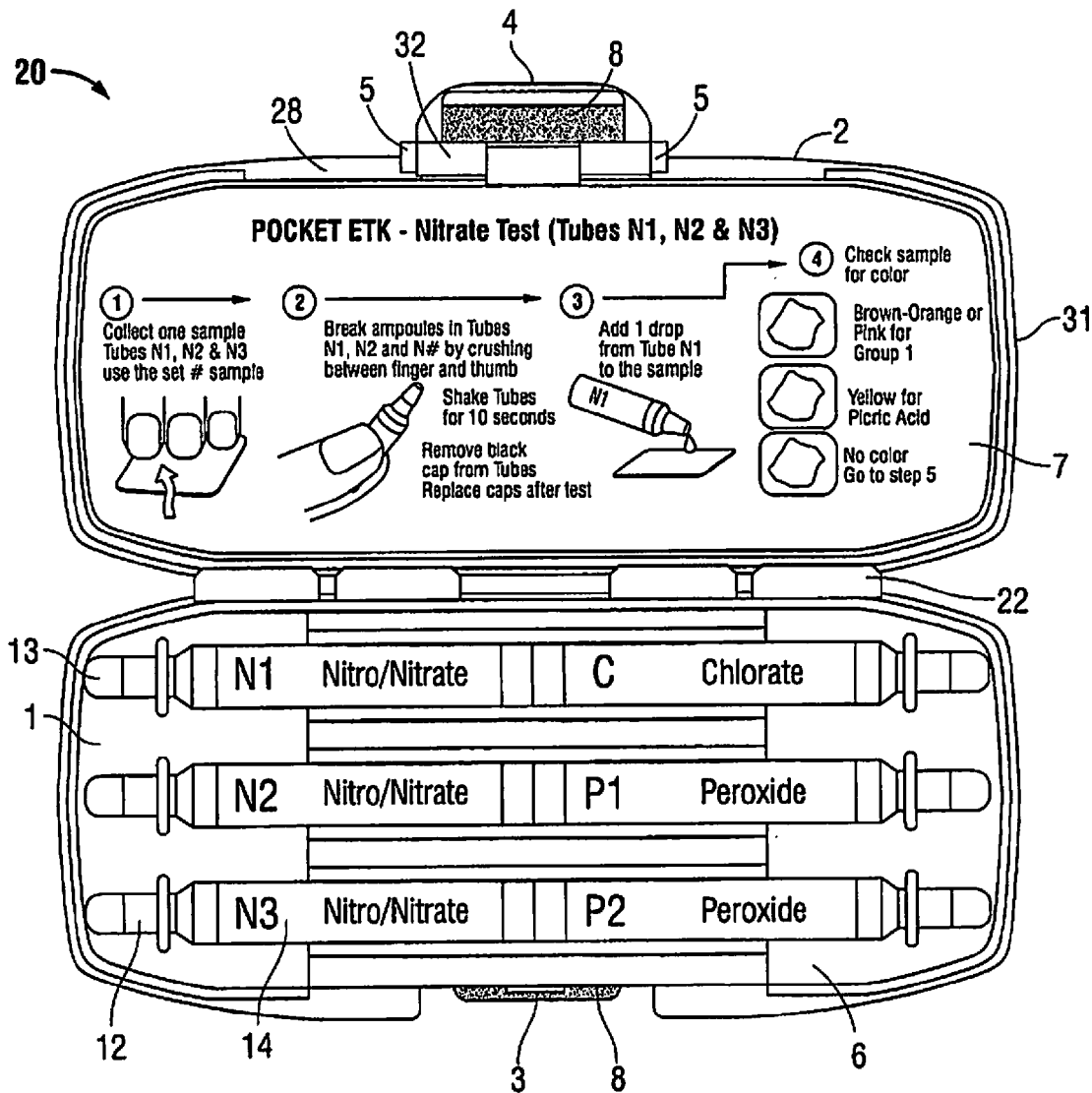
FIG. 3 is a top view of an embodiment of an ETK in accordance with the present disclosure wherein the housing is in an open position and showing a set of drip tubes seated therein.
Figure 4:
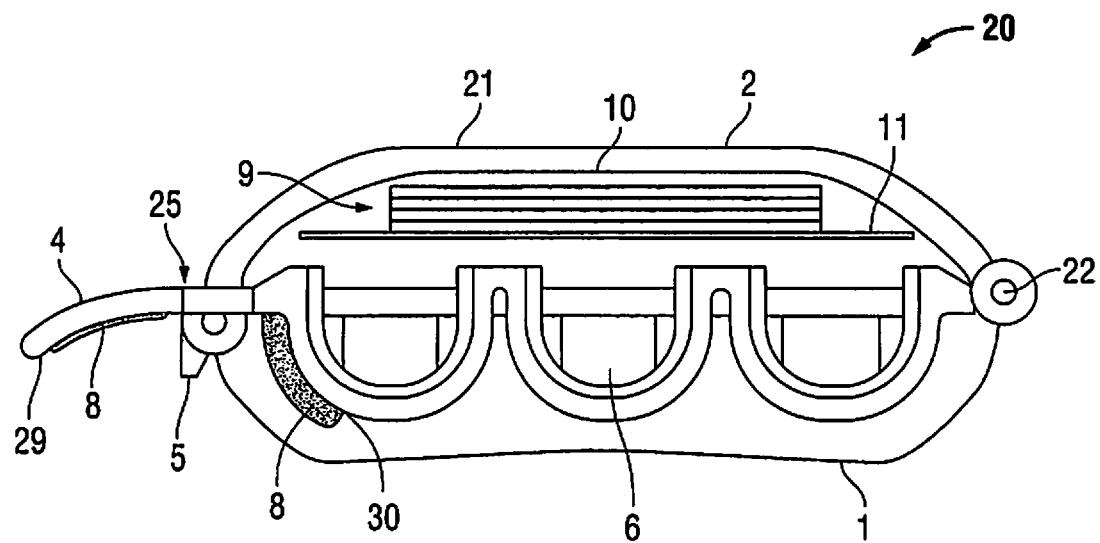
FIG. 4 is a side view of an embodiment of an ETK in accordance with the present disclosure showing a latch in an open position.
Figure 5:
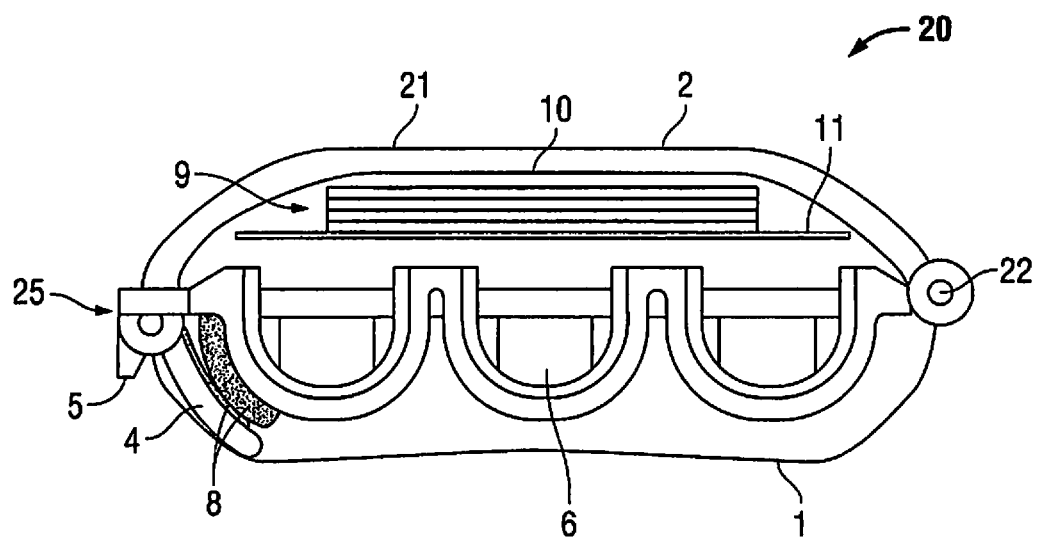
FIG. 5 is a side view of an embodiment of an ETK in accordance with the present disclosure showing a latch in a closed position.
Figure 6:
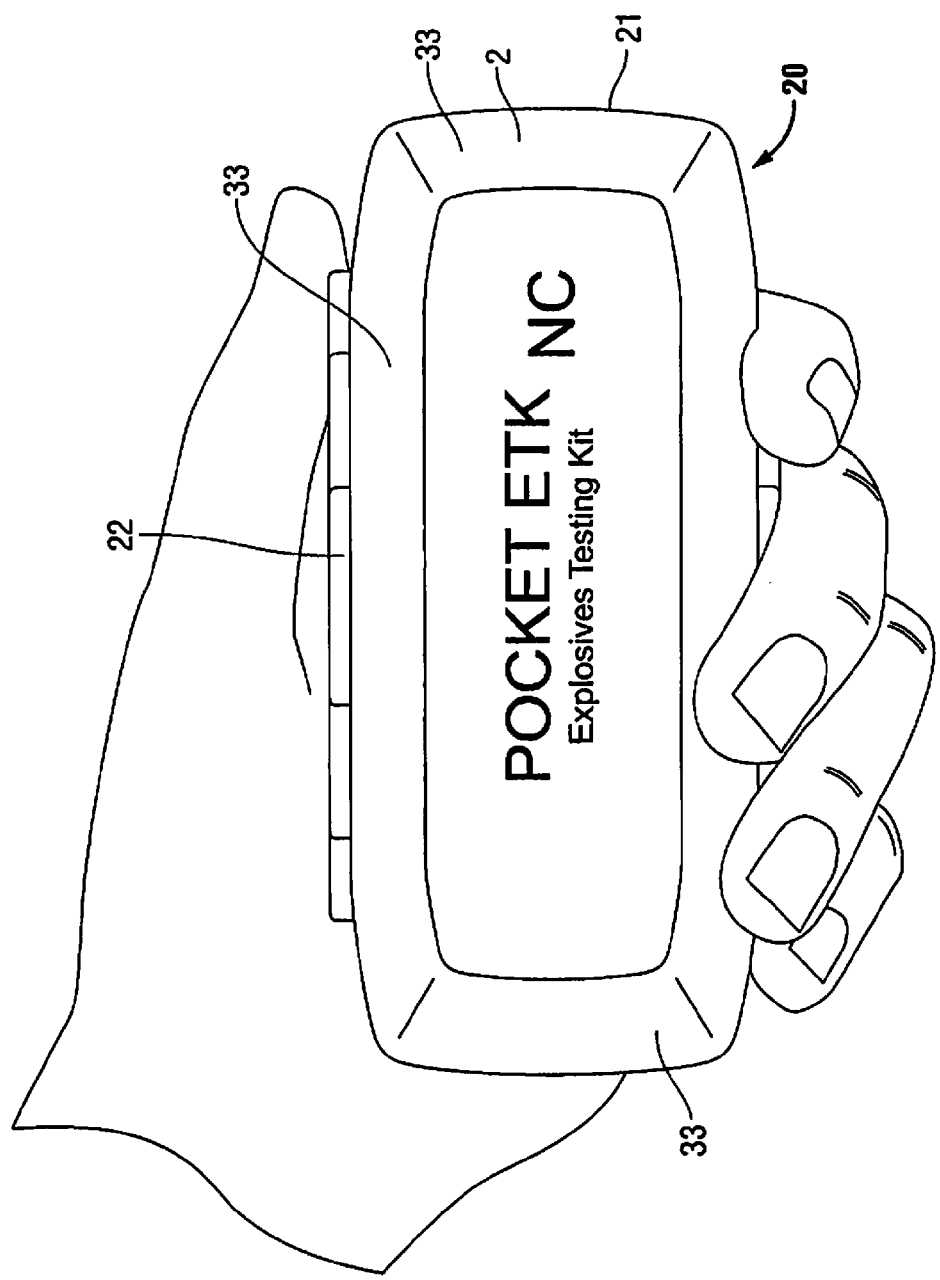
FIG. 6 is a top view of an embodiment of an ETK in accordance with the present disclosure wherein the housing is in a closed position.

With reference to FIGS. 1 and 3, an open view of an embodiment of an explosives test kit (ETK) 20 in accordance with the present disclosure is shown. Note that in FIG. 1, the ETK 20 is shown without the testing drip tubes 12 in place. ETK 20 includes a housing 21 that includes a top cover 2 and a bottom cover 1 that are joined by a hinge assembly 22. The top cover 2 and bottom cover 1 form a clamshell arrangement wherein top cover 2 and bottom cover 1 are rotatable about hinge assembly 22 between one or more open positions, examples of which are illustrated by FIGS. 1, 2, 3, and a closed position as shown in FIGS. 4, 5, and 6. Bottom cover 1 includes one or more cradles 6 formed therein that are configured to receive and retain one or more drip tubes 12. In some embodiments, cradles 6 are integrally formed with bottom cover 1 and are dimensioned to retain drip tubes 12 by frictional, snap, and/or interference fit. In some embodiments, a gasket 31 is included with top cover 2 or bottom cover 1 to form an environmental (e.g., waterproof) seal when housing 21 is in a closed position.

An instruction card 7 is fixed to top cover 2 of ETK 20, and, in some embodiments, includes one or more folding leaves upon which are depicted instructions for use of ETK 20 using any combination of graphical and textual indicia. In some embodiments, instruction card 7 may be moisture resistant and may formed from laminated card stock or polymeric card stock. In some embodiments, as shown in FIG. 1, instruction card 7 is affixed to, and folds out form, a top edge 23 of the inside of cover 2. In this configuration, the instructions may be folded out upwardly, revealing and/or enabling easy access to other components of ETK 20, as described below.

Cover 2 includes a test paper retainer 9, which may include a strap, pocket, or clip, that is configured to retain one or more test papers 10. In some embodiments, test paper retainer 9 may include one or more notches 24 defined therein that facilitates grasping and individually dispensing a sheet of test paper 10 as required. A record chart 11 is disposed on test paper retainer that is formed material that facilitates writing thereupon to enable a user to enter usage records, notes, and the like. Record chart 11 may include multiple pages in a pad-like configuration.

With reference now to FIGS. 2-5, and also with continued reference to FIG. 1, ETK 20 includes a triple-latch assembly 25 that is configured to prevent inadvertent opening of housing 21 while still facilitating rapid and easy opening when desired. In the illustrated embodiment, triple latch assembly 25 includes a first latching modality wherein a latch lever 4 associated with the top 2 rotates into positive engagement with a mating surface provide on bottom 1; a second latching modality wherein a pair of interlocking snap features engage to further facilitate latching of top 2 and bottom 1; and a third matching modality wherein a hook-and-loop fastener 8 (e.g., Velcro®) is employed to enable latch lever 4 to resist inadvertent opening. The disclosed triple latch system can be used for any kit or container that requires a secure latching system.

In more detail, triple-latch assembly 25 includes a latch lever 4 hingedly coupled to top 2 which includes several features which cooperate with features of bottom 1 to facilitate effective latching of top 2 to bottom 1. Latch lever 4 includes at least one stop rib 5. In some embodiments, latch lever 4 and stop rib 5 may be integrally formed. The first latching modality is best seen in FIGS. 4 and 5, stop rib 5 is fixedly coupled to and rotates with latch lever 4 as latch lever 4 is rotated between an open position, as shown in FIG. 4, and a closed position, as shown in FIG. 5. As latch lever 4 rotates into a closed position, stop rib 5 rotates into engagement with a striker face 26 provided on an underside of a latch face 27 of bottom cover 1, thereby securing top 2 in a closed position with respect to bottom cover 1. Conversely, when opening, as latch lever 4 is rotated into an open position, stop rib 5 rotates away from striker face 26, thereby disengaging top cover 2 from bottom cover 1 and enabling housing 21 to be moved into an open position.

A second latching modality is achieved by the engagement of snap rib 3 which protrudes from latch face 27 and engages with a ridge 28 extending from top cover 2. In some embodiments (for example, where top 2 and bottom 1 are formed from resilient polymeric material) as top cover 2 and bottom cover 1 are brought into closed position, snap rib 3 and ridge 28 come into contact, providing resistance to achieving full closure of top 2 and bottom 1. As the user continues to apply closing force to top cover 2 and bottom cover 1, snap rib 3 and ridge 28 begin to deflect under pressure and eventually, bypass one another such that snap rib 3 "snaps" past ridge 28 into a fully closed position resting on an upper surface of ridge 28, and thereby retaining housing 21 in a closed position. Conversely, to open housing 21, a user applies opening force to top cover 2 and bottom cover 1, by, e.g., grasping an unhinged portion of top cover 2 and pulling it away from bottom cover 1 until snap rib 3 "unsnaps" from ridge 28 thereby enabling housing 21 to be moved into an open position.

A third latching modality is achieved by pair of mating hook and loop fasteners 8 that are disposed on an inner surface 29 of latch lever 4, and a corresponding mating surface 30 provided on an underside of bottom cover 1. Hook and loop fasteners 8 are configured to enable latch lever 4 to be held securely in a closed position, as best shown in FIG. 5. As latch lever 4 is brought from an open position, as shown in FIG. 4, into a fully-latched position as shown in FIG. 5, hook end loop fasteners 8 engage one another and hold latch lever 4 in the fully latched position. Conversely, to release latch lever 4, a user applies opening force to latch lever 4 by rotating it in an upward direction (or, as seen in the FIG. 5 view, a clockwise direction) to overcome the gripping force of hook and loop fasteners 8, to enable latch lever 4 to swing into an open position as seen in FIG. 4.

During use, the three latching modalities of triple-latch assembly 25 described above combine to facilitate an easy to use, yet secure and redundant, ETK latching function which helps ensure successful and reliable results in the testing theatre by preventing the inadvertent and untimely opening of the ETK 20 and spillage and/or damage of the ETK 20 components.

With reference to FIG. 3, a top view of a fully opened ETK housing 22 is shown. One or more testing drip tubes 12 are secured within their respective cradles. In the illustrated embodiment, six testing drip tubes 12 may be fit into three cradles 6 formed into the case bottom 1. In some embodiments, an ETK in accordance with the present disclosure may include greater than six drip tubes 12 or fewer than six drip tubes 12, and/or may include greater than three cradles 6 or fewer than three cradles 6. Each drip tube 12 includes a corresponding drip tube cap 13, which may be selectively fixed to the dispensing end of the drip tubes 12 by a friction fit, threaded fastening, and the like, and in some embodiments may include a safety seal (not explicitly shown) provided to reduce the likelihood of tampering and which must be broken before a first use. The caps 13 minimize leakage and/or evaporation of the liquid reagents which are stored in the testing drip tubes 12. Each drip tub 12 includes a corresponding color coded label 14 that are arranged such that the end user can clearly see the markings and identify which testing drip tube 12 should be used, and which may include simplified instructions for use, and which may include a positive results chart.

FIG. 4 shows a cross-section of a closed housing 21 with the latch lever 4 and stop rib 5 rotated in the open position and where the hook and loop fasteners 8 are not engaged. The test papers 10 are positioned within the test paper pocket 9 which is fixed to the underside of the top cover 2 as described above. The instruction card 7 is folded and fixed to the underside of top cover 2. In the illustrated embodiment, cradles 6 are formed in the case bottom 1 such that there is enough space between them for an end-user to easily extract drip tubes 12 from the housing 21.

FIG. 5 shows a cross-section of the case in the fully closed position, where all three components of the triple latch system are engaged, i.e., the ridge 28 of top cover 2 is engaged with the undercut snap rib 3, the latch lever 4 is rotated to a fully closed position closed to engage the hook and loop fasteners 8, and the stop rib(s) 5 of latch lever 4 are rotated under the top edge of the bottom cover 1 and engaged with striker face 26.

In some embodiments, the housing 21 is formed from polymeric materials, which may be rigid or semi-rigid plastic. For example, and without limitation, housing 21 may be formed from polypropylene (PP), polyethylene (PE), high density polyethylene (HDPE), acrylonitrile butadiene styrene (ABS), or combinations thereof. The hinge 22 joining bottom cover 1 and top cover 2 may incorporate a hinge assembly having a hinge knuckle and a hinge pin (not explicitly shown) and/or may include a living hinge. Latch lever 4 may be joined to top cover 2 by a hinge assembly 32 which may include a hinge knuckle and a hinge pin (not explicitly shown) and/or may include a living hinge. The top cover 2 secures to the bottom cover 1 with a triple latch system. The first aspect of the triple latch system includes undercut snap rib 3 located on the bottom cover that is configured to engaging with an under surface of the top cover 2. The undercut snap 3 closes the top cover 2 onto the bottom cover. The second aspect of the triple latch system includes a hook and loop closure 8 disposed between the latch lever 4 and a mating surface 30 of the bottom cover 1. In use, the hook and loop fastener 8 prevents latch 4 from flipping open. The third aspect of the triple latch system includes the stop rib(s) 5 associated with the latch lever 4. When latch lever 4 is in a closed position, the stop rib 5 engages the bottom cover 1 to help prevent the top cover 2 from popping open even if the undercut snap 3 releases, thereby keeping the stop rib 5 engaged with the bottom cover 1.

In another aspect of an ETK in accordance with the present disclosure, an inner surface 34 of the top cover 2 includes a contoured portion 33 that is configured to prevent the test papers 10 from falling out of the top cover 2 when turned upside down, regardless if the case is open or closed. In some embodiments, the contoured portion 33 is concave and deep enough to prevent even one test paper 10 from falling out, while still enabling the test papers 10 to be easily removed from the test paper pocket 9. In embodiments, the depth of the contoured portion is in the range of about 1/16 inches to about 1/2 inches. In another aspect, the test papers 10 include a plastic backing to prevent leakage of reagent through the paper. In yet another aspect, the test papers 10 include an adhesive (e.g., "tacky") test surface that is configured enhance sample collection. In still another aspect, the test papers 10 include a protective cover that prevents contamination prior to use.

In use, a user may lift the latch lever 4 to release the triple latch system and open the housing 21. The instruction card 7 may be extended from the top cover 2 and read by the user. A test kit in accordance with the present disclosure may include a variety of drip tubes 12, each of which may be adapted to test for a specific substance, or combinations of substances. For example, and without a limitation, a drip tube 12 in accordance with the present disclosure may include reagents or other test compounds adapted to detect the presence of nitro/nitrate-based explosives (such as, without limitation, TNT, DNT, TNB, tetryl, picric Acid, NG, PETN, RDX, HMX, NC, C4, Semtex, smokeless powder, ammonium nitrate, potassium nitrate, black powder, and ANFO); chlorate-based explosives (such as, without limitation, inorganic chlorates, hypochlorite, and bromates); peroxide-based explosives (such as, without limitation, organic peroxides, TATP, DADP, and HMTD); ammonium; urea nitrate; and drugs (such as, without limitation, THC, opiates, cocaine, methamphetamine, oxycodone, MDMA, LSD, mescaline, psilocybin, scopolamine, etc.)

The user removes a sheet of test paper 10 from the test paper pocket 9, and wipes the surface to be tested with the test paper. The user removes the test drip tube 12 corresponding to the desired substance for which the test is being conducted from its respective cradles, removes the drip tube cap 13, and drips the reagents (e.g., detection fluid) onto the test papers in accordance with the instruction card. A resultant change in the color of the test paper is compared to the a color chart provided on color coded label 14 and/or on the instruction card 7, and the outcome of the test is determined by color match.

After use, the drip tube cap 13 is re-affixed to the test drip tube 12, the test drip tube 12 is returned to its cradle 6, the instructions 7 are folded into its original position, the top cover 2 and bottom cover 1 are snapped closed, and the latch lever 4 is rotated downward to secure the hook and loop fastener 8 and engage the stop rib 5, thereby securing the ETK in the closed position.

Advantageously, the disclosed triple-latch system enables the housing 22 to be securely closed without extra effort from the end-user. First, the top cover 2 is snapped shut onto the bottom cover 1, then the latch lever 4 is rotated down which simultaneously engages the hook and loop fastener 8 and the stop rib 5, preventing the housing 21 from popping open during storage and carrying of the ETK 20. The hook and loop fastener 8 keeps the latch lever 4 firmly seated down which keeps the stop ribs 5 fully engaged with striker face 26 of bottom cover 1.

Another advantageous and unique feature of the triple-latch system is that all three latching modalities are opened simultaneously when the latch lever 4 is rotated up. In more detail, the rotating opening action applied to latch lever 4 pulls the hook and loop fastener 8 apart, disengages the stop ribs 5 from striker face 26 of bottom cover 1, and applies enough force to easily disengage undercut snap rib 3. The top cover 2 opens along a horizontal axis defined by hinge 22 and rotates open into a flat orientation for maximum stability during use, while also providing maximum visual contact with and physical access to the test components and instructions. The top cover 2 and bottom cover 1 of housing 22 are configured to retain all ETK components (e.g., test papers 10, drip tubes 12) such that they will not inadvertently fall out if the case is turned upside down, jostled, mishandled, etc. The fold-out instructions 7 are securely fixed to the top cover 2, preventing the instructions 7 from being separated from the housing 22 and preventing loss. The top cover 2 is contoured with a concave inner surface configured to contain any number of test papers 10 which may be stored in test paper pocket 9 such that no test papers 10 will fall from the housing 21, regardless of orientation, while still permitting the test papers 10 to be easily removed by the end-user. The cradles 6 of bottom cover 1 frictionally fit the drip tubes 12 such no drip tubes 12 will fall out of the housing 21, yet are dimensioned to enable the end-user to easily select and remove one or more drip tubes 12 for use. In addition the testing drip tubes 12 are color-coded to match the test paper 10 color indicating positive result, and include simplified instructions on the tube label 14 allowing a novice user to operate the ETK 20 with minimal or no training. The testing drip tube caps 13 minimize evaporation and leakage of used testing drip tubes, allowing for multiple uses of the testing drip tubes 12.

In another aspect, a method of manufacturing a portable ETK is disclosed. The housing 21 is formed from a rigid or semi-rigid material. In some embodiments, the bottom cover 1 and/or top cover 2 may be formed by injection molding. In some embodiments, bottom cover 1 and top cover 2 are integrally formed by injection molding wherein hinge 22 is a living hinge joining bottom cover 1 and top cover 2. In some embodiments, bottom cover 1 and top cover 2 are formed by injection molding and include articulating main hinge adapted to receive a metal hinge pin and/or may be configured as a snap hinge such that the cover can rotate open 180 degrees and lay flat open on a flat surface. The mold is configured to form a contoured portion 33 of the top cover 2 that is adapted to accept the test papers 10 and prevent test papers 10 from falling out inadvertently. Cradles 6 are integrally formed into the bottom cover by, e.g., injection molding.

The latch lever 4 may be integrally formed with top cover 2 by, e.g., injection molding and/or may be coupled to top cover 2 with a metal hinge pin or with a snap hinge. Stop rib 5 may be integrally formed as part of latch lever 4 by, e.g., injection molding, and/or may be joined to latch lever 4 by ultrasonic welding, adhesive, or mechanical coupling.

A pair of mating hook and loop fasteners 8 are cut to size and applied to the underside of latch lever 4 and mating surface 30 of bottom cover 1. In some embodiments, hook and loop fasteners are applied to latch lever 4 and mating surface 30 of bottom cover 1 using high-strength adhesive. In some embodiments, hook and loop fasteners are applied to latch lever 4 and mating surface 30 of bottom cover 1 using ultrasonic welding.

Fold-out instructions 7 are applied to an inside surface of top cover 2 using adhesive, tape, or other suitable faster. In some embodiments, a bottom portion of instructions 7 may be folded and fixed to top cover 2 to form test paper pocket 9. The appropriate testing tube labels 14 are fixed to corresponding drip tubes 12, and the drip tubes 12 are inserted into the cradles 6 as desired.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A portable substance detection field test kit, comprising:
    a top cover having a hinge side, a latch side, and a ridge extending from the latch side;
    a bottom cover having a hinge side, a latch side, a cradle on an inner surface thereof configured to selectively retain a drip tube, and a latch face extending from the latch side of the bottom cover having a snap rib protruding therefrom, wherein the top cover and bottom cover are joined by a hinge along the respective hinge sides thereof forming a housing having an open position wherein the latch sides of the top cover and bottom cover are separated, and a closed position wherein the latch sides of the top cover and bottom cover are joined;
    a drip tube;
    a sheet of test paper adapted to collect a substance sample; and
    a latch assembly, comprising:
        a latch lever having an open position and a closed position;
        a stop rib operatively associated with the latch lever and configured to engage the underside of the latch face when the latch lever is in a closed position; and
        a first hook and loop fastener and a mating second hook and loop fastener, wherein the first hook and loop fastener is disposed on an inner surface of the latch lever and the second hook and loop fastener is disposed on a mating surface of the bottom cover, wherein the first and second hook and loop fasteners engage when the latch lever is in a closed position, and
        wherein the latch lever, when moved from the closed position to the open position, simultaneously causes the first hook and loop fastener to disengage with the second hook and loop fastener and unsnaps the snap rib causing the latch side of the top cover to separate from the latch side of the bottom cover.

2. The portable substance detection field test kit in accordance with claim 1, wherein when the housing is in the closed position the snap rib of the bottom cover and the ridge of the top cover are cooperatively engaged.

3. The portable substance detection field test kit in accordance with claim 1, wherein the latch lever is joined to the top cover by a hinge.

4. The portable substance detection field test kit in accordance with claim 1, further includes a gasket disposed between the top cover and the bottom cover.

5. The portable substance detection field test kit in accordance with claim 1, wherein the top cover further includes a contoured portion defined on an inner surface thereof.

6. The portable substance detection field test kit in accordance with claim 5, wherein the contoured portion is concave.

7. The portable substance detection field test kit in accordance with claim 6, wherein the depth of the concave contoured portion is in a range of about 1/16 inches to about 1/2 inches.

8. The portable substance detection field test kit in accordance with claim 1, wherein the drip tube contains a reagent solution configured to expose the presence of a targeted substance by causing an initial color of a test sample to change to a predetermined color when the reagent solution is applied to the test sample.

9. The portable substance detection field test kit in accordance with claim 8, wherein the drip tube includes a label having a color indicating the predetermined color.

10. The portable substance detection field test kit in accordance with claim 8, wherein the targeted substance is selected from the group consisting of TNT, DNT, TNB, tetryl, picric Acid, NG, PETN, RDX, HMX, NC, C4, Semtex, smokeless powder, ammonium nitrate, potassium nitrate, black powder, ANFO, inorganic chlorates, hypochlorite, bromates, organic peroxides, TATP, DADP, and HMTD, ammonium; urea nitrate, THC, an opiate, cocaine, methamphetamine, oxycodone, MDMA, LSD, mescaline, psilocybin, and scopolamine.

11. A portable container, comprising:
a top cover having a hinge side, a latch side, and a ridge extending from the latch side of the top cover;
a bottom cover having a hinge side, a latch side, and a latch face extending from the latch side of the bottom cover having a snap rib protruding from the latch face, wherein the top cover and bottom cover are joined by a hinge along the respective hinge sides thereof forming a housing having an open position wherein the latch sides of the top cover and bottom cover are separated, and a closed position wherein the latch sides of the top cover and bottom cover are joined; and
a latch assembly, comprising:
a latch lever having an open position and a closed position;
a stop rib operatively associated with the latch lever and configured to engage the underside of the latch face when the latch lever is in a closed position;
a first hook and loop fastener and a mating second hook and loop fastener, wherein the first hook and loop fastener is disposed on an inner surface of the latch lever and the second hook and loop fastener is disposed on a mating surface of the bottom cover, wherein the first and second hook and loop fasteners engage when the latch lever is in the closed position,
wherein the latch lever, when moved from the closed position to the open position, simultaneously causes the first hook and loop fastener to disengage with the second hook and loop fastener and unsnaps the snap rib causing the latch side of the top cover to separate from the latch side of the bottom cover.

12. The portable container in accordance with claim 11, wherein when the housing is in the closed position the snap rib of the bottom cover and the ridge of the top cover are cooperatively engaged.

13. The portable container in accordance with claim 11, wherein the latch lever is joined to the top cover by a hinge.

14. The portable container in accordance with claim 11, further including a gasket disposed between the top cover and the bottom cover.

15. The portable container in accordance with claim 11, wherein the top cover further includes a contoured portion defined on an inner surface thereof.

16. The portable container in accordance with claim 15, wherein the contoured portion is concave.

17. The portable container in accordance with claim 16, wherein the depth of the concave contoured portion is in a range of about 1/16 inches to about 1/2 inches.

18. A method of conducting a test to detect the presence of a targeted substance, comprising:
providing a portable substance detection field test kit, comprising:
a top cover having a hinge side and a latch side;
a bottom cover having a hinge side, a latch side, a cradle on an inner surface of the bottom cover configured to selectively retain a drip tube, and a latch face extending from the latch side thereof having a snap rib protruding from the latch face, wherein the top cover and bottom cover are joined by a hinge along the respective hinge sides thereof forming a housing having an open position wherein the latch sides of the top cover and bottom cover are separated, and a closed position wherein the latch sides of the top cover and bottom cover are joined;
a drip tube containing a reagent solution configured to expose the presence of a targeted substance by causing an initial color of a test sample to change to a predetermined color when the reagent solution is applied to the test sample;
a sheet of test paper adapted to collect a substance sample; and
a latch assembly, comprising:
a latch lever having an open position and a closed position;
a stop rib operatively associated with the latch lever and configured to engage the underside of the latch face when the latch lever is in the closed position; and
a first hook and loop fastener and a mating second hook and loop fastener, wherein the first hook and loop fastener is disposed on an inner surface of the latch lever and the second hook and loop fastener is disposed on a mating surface of the bottom cover, wherein the first and second hook and loop fasteners engage when the latch lever is in the closed position,
wherein the latch lever, when moved from the closed position to the open position, simultaneously causes the first hook and loop fastener to disengage with the second hook and loop fastener and unsnaps the snap rib causing the latch side of the top cover to separate from the latch side of the bottom cover;
removing a sheet of test paper from the pocket;
wiping a surface to be tested with the test paper;
removing the drip tube from the cradle;
dispensing the reagent solution from the drip tube onto the test paper;
observing a color change on the test paper; and
concluding that the targeted substance is present in the test sample if the color of the test paper changes to the predetermined color.

19. The method of conducting a test to detect the presence of a targeted substance, in accordance with claim 18, further including:
   comparing the color change of the test paper to a color sample provided on a label affixed to the removed one of the plurality of drip tubes.

20. The method of conducting a test to detect the presence of a targeted substance, in accordance with claim 18, wherein the targeted substance is selected from the group consisting of TNT, DNT, TNB, tetryl, picric Acid, NG, PETN, RDX, HMX, NC, C4, Semtex, smokeless powder, ammonium nitrate, potassium nitrate, black powder, ANFO, inorganic chlorates, hypochlorite, bromates, organic peroxides, TATP, DADP, and HMTD, ammonium; urea nitrate, THC, an opiate, cocaine, methamphetamine, oxycodone, MDMA, LSD, mescaline, psilocybin, and scopolamine.

* * * * *